United States Patent [19]

Nishijima et al.

[11] Patent Number: 4,942,364
[45] Date of Patent: Jul. 17, 1990

[54] MOISTURE AND DEW-DETECTION SENSOR

[75] Inventors: Jun-ichi Nishijima, Katano; Minoru Fukui, Suita, both of Japan

[73] Assignee: Asahi Kasei Kogyo Kabushiki Kaisha, Osaka, Japan

[21] Appl. No.: 310,179

[22] Filed: Feb. 14, 1989

[30] Foreign Application Priority Data

Feb. 19, 1988 [JP] Japan .................................. 63-35394
May 16, 1988 [JP] Japan ................................. 63-117064

[51] Int. Cl.$^5$ ............................................. G01R 27/08
[52] U.S. Cl. ................................. 324/696; 73/336.5; 324/694; 340/604; 338/35
[58] Field of Search ............. 324/65 P, 65 R, 525; 340/604, 602; 73/336.5, 335; 338/35

[56] References Cited

U.S. PATENT DOCUMENTS

| | | | |
|---|---|---|---|
| 2,064,651 | 12/1936 | Fiene | 324/65 P |
| 2,742,541 | 4/1956 | Bunting | 324/65 P |
| 3,383,863 | 5/1968 | Berry | 324/65 P |
| 3,703,696 | 11/1972 | Browall et al. | 73/335 X |
| 3,821,093 | 6/1974 | Carron et al. | 73/335 X |
| 4,373,391 | 2/1983 | Johnson | 73/335 |
| 4,677,416 | 6/1987 | Nishimoto et al. | 338/35 |

FOREIGN PATENT DOCUMENTS 57-211051 12/1982 Japan .
59-43345 3/1984 Japan .
60-200152 10/1985 Japan .

*Primary Examiner*—Reinhard J. Eisenzopf
*Assistant Examiner*—Robert W. Mueller
*Attorney, Agent, or Firm*—Finnegan, Henderson, Farabow, Garrett & Dunner

[57] ABSTRACT

A moisture and dew-detection sensor comprises a fabric and a moisture sensing resistive substance adhered in a substantially continued and dispersed state to the fabric, and a plurality of fine voids are formed in the moisture and dew-detection sensor. A response time and an accuracy of the sensor in accordance with the present invention are superior due to the existence of the plurality of voids.

10 Claims, 19 Drawing Sheets

Fig. 11(a)
Fig. 11(b)
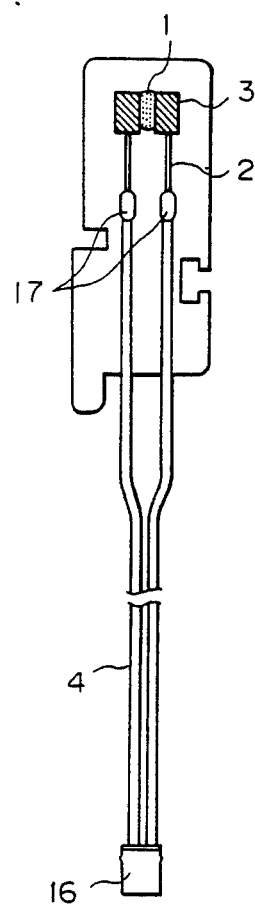
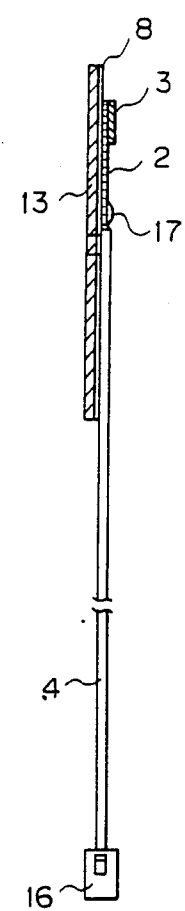

MOISTURE AND DEW-DETECTION SENSOR

BACKGROUND OF THE INVENTION

1. Field of the Invention

The present invention relates to a moisture and dew-detection sensor capable of detecting a change of atmospheric humidity or dew condensation on a surface of a substance.

2. Description of the Prior Art

Dew condensation is a problem in the fields of a precision electrical devices, automobiles, air conditioning systems, warehouses and domestic equipment, etc., and there is a strong demand for a sensor able to accurately detect a high humidity or dew condensation state.

For example, when dew condensation is generated on a cylinder of a rotary head for recording or playing back a magnetic tape in a video tape recorder, a digital audio tape deck or the like, roll-in or a breakage of the magnetic tape, on damage to a device may occur, and therefore various types of dew condensation sensors are arranged in the device.

A dew condensation sensor comprising a moisture sensing resistive substance in which electric conductive powders are dispersed in a moisture absorption high polymer having characteristic of an expansion of a volume thereof by moisture absorption, and a comb-shaped electrode formed on an isolated base plate and covered by the moisture sensing resistive substance in a state of a film having a thickness of from 5 $\mu$m to several tens of $\mu$m was disclosed in Japanese Unexamined Patent Publication (Kokai) No. 57-2110511 or the like, and changes of a resistance value of this dew condensation sensor are large in a high humidity region, to thereby detect a high humidity state and a state in which dew condensation is easily generated, i.e., a state approaching a relative humidity of 100%.

Nevertheless, since the comb-shaped electrode is arranged just below a thin film of the moisture sensing resistive substance, to bring the sensitivity of the sensor upto a practical level, in this type of the dew condensation sensor, when a large quantity of dew is generated by dew condensation, the amount of water which a portion of the film of the moisture sensing resistive substance positioned just below the dew can absorb is immediately exceeded, and excess water not absorbed by the film remains on the surface of the film as water. When the dew condensation is dissolved, the speed of evaporation of moisture in the film is different at a portion of the film covered by the water and than at a portion of the film not covered by the water, so that the moisture in the portion of the film not covered by the water was first evaporated and the value of the resistance of the dew-detection sensor reduced. Therefore this type of the dew-detection sensor caused an error in the detection of humidity when dissolving the dew. Further, when the amount of dew condensation is small, the speed of response of the sensor is slow. To obtain a film having a uniform thickness in this dew-detection sensor, the film must be thick. Water condensed on a surface of the film is absorbed into this film, and thus some time is required to evaporate the water from inside the film, and unavoidably, the response speed when a generation or a dissolving of dew condensation is detected is too slow.

Japanese Unexamined Patent Publication (Kokai) No. 59-43345 disclosed a dew-detection sensor having a detection portion constituted by electric conductive particles provided uniformly on a surface of a moisture absorption fiber. In this dew-detection sensor, the moisture absorption fiber contracts or expands with an absorbent or an adhesive of a moisture adsorption used to make the moisture absorption sensor by change of the humidity. Therefore, when a large amount of water is generated by the dew condensation, the pater is absorbed sequentially into the fiber, and even if a dew condensing state in an atmosphere is eliminated, the dew-detection sensor still maintains the dew condensing state thereof. In particular, when a fiber of a cellulose group is used, since a retention of water molecules caused by a hydrogen bond in the fiber is strong, the fiber is not easily dried, and thus it is impossible to perform an accurate detection of the dew condensation.

SUMMARY OF THE INVENTION

A first object of the present invention is to provide a moisture and dew-detection sensor having a quick response speed upon a change of humidity and a low amount of a dew condensation, and a large change of a value of resistance to a change of a humidity, and not having a time lag between a time that a dew condensation is actually generated or dissolved on a substance to be detected and a time that the moisture and dew-detection sensor detects a generation or a dissolving of the dew condensation.

A second object of the present invention is to provide a compact and a light moisture and dew-detection sensor device including the moisture and dew-detection sensor in accordance with the present invention.

A third object of the present invention is to provide a moisture and dew-detection sensor module including the moisture and dew-detection sensor device in accordance with the present invention and able to use same even if an amplifier circuit, a noise filter circuit or the like is not provided.

In accordance with the present invention, the first object can be obtained by a moisture and dew-detection sensor comprised of a fabric and a moisture sensing resistive substance adhered in a substantially continuous and dispersed state onto the fabric, and including a plurality of fine voids in the moisture and dew-detection sensor.

The second object of the present invention can be attained by a moisture and dew-detection sensor device comprised of the moisture and dew-detection sensor in accordance with the present invention, a base plate supporting the moisture and dew-detection sensor, and at least two electrodes connected to the moisture and dew-detection sensor and used to measure an electrical resistance of the moisture and dew-detection sensor.

Preferably, the moisture and dew-detection sensor further includes means for fixing the moisture and dew-detection sensor on a substance to be detected.

The third object of the present invention can be attained by a moisture and dew-detection sensor module comprised of the moisture and dew-detection sensor device in accordance with the present invention, and a circuit capable of detecting a change of an electrical resistance and outputting the change of the electrical resistance as a signal of an electric voltage or an electric current.

Further, a moisture and dew-detection sensor system can be obtained by further providing means of measuring a time when the dew is generated, an alarm device using sound or light, and means of activating a heated fan or the like in accordance with a signal from the moisture and dew-detection sensor module.

BRIEF DESCRIPTION OF THE DRAWINGS

FIG. 10(a)-10(c) illustrate a typical moisture and dew-detection sensor device in accordance with the present invention, wherein FIG. 10(a) is a front view, FIG. 10(b) is side view, and FIG. 10(c) is a cross sectional view;

FIGS. 11(a) and 11(b) illustrate another typical moisture and dew-detection sensor device in accordance with the present invention, wherein FIG. 11(a) is a front view and FIG. 11(b) is a side view;

FIGS. 12(a) and 12(b) illustrate an example of the moisture and dew-detection sensor device in accordance with the present invention equipped with a cover having a water resistance, an oil resistance and an air permeability, wherein FIG. 12(a) is a perspective view and FIG. 12(b) is a cross sectional view;

FIGS. 17(a) and 17(b) illustrate an example of a moisture and dew-detection sensor system, i.e., an information apparatus capable of warning of a generation of a mist on a surface of a front glass of an automobile, wherein FIG. 17(a) is a cross sectional view of the apparatus, and FIG. 17(b) is a view illustrating the apparatus when attached to the front glass;

FIGS. 21(a) and 21(b) illustrate other example of a moisture and dew-detection sensor system, i.e., a pen-type drying information device, wherein FIG. 21(a) is a cross sectional view of the pen-type drying information device and FIG. 21(b) is a view illustrating the device when inserted into a shirt pocket.

DESCRIPTION OF THE PREFERRED EMBODIMENTS

The present invention will now be described in detail with reference to the accompanying drawings illustrating embodiments of a moisture and dew-detection sensor, a moisture and dew-detection sensor device, and a moisture and dew-detection sensor module or the like, in accordance with the present inventions.

Figure 1:
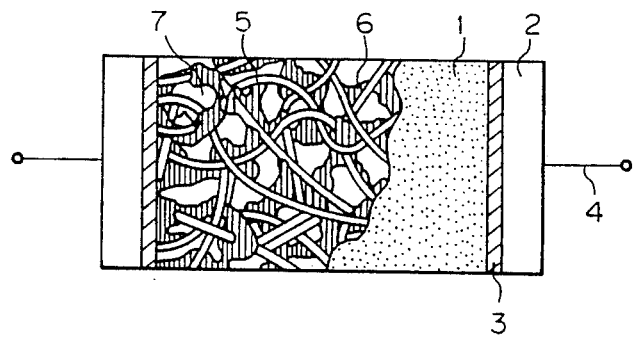
FIG. 1 is a plan view illustrating a moisture and dew-detection sensor device in accordance with the present invention and including a partially cut out view illustrating in an enlarged state an example of a constitution of the moisture and dew-detection sensor.

FIG. 1 shows an embodiment of a moisture and dew-detection sensor device in accordance with the present invention. In FIG. 1, the moisture and dew-detection sensor device comprises a moisture and dew-detection sensor 1 by which humidity or a generation of dew condensation is detected as a change of an electrical resistance, thereof, wherein an electrode 2 is connected through a conductive connecting portion 3 to the moisture and dew-detection sensor 1. An electrical signal is output through a conductive line 4. As shown in a cut out view of FIG. 1, the moisture and dew-detection sensor 1 comprises a nonwoven fabric constituted of a plurality of fibers 5 and a moisture sensing resistive substance 6 adhered in a substantially continuous and dispersed state to the fiber 5 of the nonwoven fabric, and a plurality of fine voids 7 are formed in the sensor 1.

In the moisture and dew-detection sensor in accordance with the present invention, the moisture sensing resistive substance must have a larger surface thereof in the fabric and be adhered in a continuously dispersed state to the fabric. Since the moisture and dew-detection sensor has a fine porous structure, as described herebefore, water of dew condensation can rapidly be diffused into the fabric by a capillary action of the voids 7, and thus the dew condensation detected. Therefore, a response speed when detecting a generation of dew condensation is fast. When the dew condensation is dissolved, since water held on the surface of the sensor and/or absorbed in the sensor 1 can be rapidly evaporated or diffused due to the voids and large surface of the moisture sensing resistive substance, a response speed of detecting a dissolution of the dew condensation is also fast.

Further when a large quantity of water is formed by dew condensation or the dew state continuous for a long time, excess water which the moisture sensing resistive substance 6 cannot absorb can be held by the voids 7 of the sensor 1.

Figure 2:
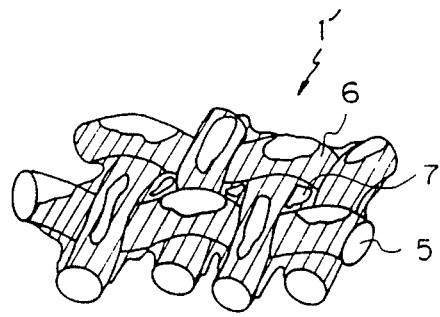
FIG. 2 is a perspective view of another example of a moisture and dew-detection sensor using a woven fabric as a fabric in accordance with the present invention.

FIG. 2 shows another embodiment of the moisture and dew-detection sensor in accordance with the present invention. In this embodiment, a fabric woven from monofilaments 5 is used, and a plurality of voids 7 are present in the moisture sensing resistive substance 6 adhered to the monofilament 5 of the woven fabric. When a multifilament, a textured yarn, a spun yarn or the like constituted by many single filaments or fibers is used in place of the monofilament, it is possible to provide many voids in the warp yarns and weft yarns of the woven fabric.

A woven fabric having an optional weave, e.g., a plain weave, a twill weave, a satin weave or the like, a knitted fabric, including a warp knitted fabric and a weft knitted fabric, and a nonwoven fabric, can be used for the fabric in the moisture and dew-detection sensor.

Various type of yarn including monofilament, multifilament, spun yarn, split yarn or the like can be used as the yarn constituting the fabric in the moisture and dew-detection sensor. But, to hold the moisture sensing resistive substance in the continuous and dispersed state on larger surfaces of the fibers, preferably a multifilament is used, in particular a multifilament constituted by finer single filaments. Further, to enlarge the surface of fiber and increase the adhesion thereof with the moisture sensing resistive substance, micro concave-convex portions can be formed on the surface of the fiber by applying a surface partial removal treatment.

The nonwoven fabric is a fiber sheet manufactured by a melt blowing method, a flash spinning method, a spun bond method, a felting method, a paper making method or the like, provided uniformly with a plurality of voids, and having a multi layer structure. Since the melt blowing method, the flash spinning method and the spun bond method can directly form the fiber sheet from a molten polymer, a nonwoven fabric manufactured from an extra fine fiber and having a large surface of the fiber therein and a fine porous structure can be prepared at a low cost.

A diameter of a fiber used in the fabric of the moisture and dew-detection sensor should be 30 μm or less, preferably 15 μm or less, more preferably 5 μm or less. When a fiber having a small diameter is used, the dispersion of the fibers is improved, and thus the voids in the fine porous structure formed by the fibers become uniform and the moisture sensing resistive substance can be held in a uniformity dispersed state in the fabric. By using such a fabric, a sensor having a quick response speed for a change of humidity and a generation or dissolution of the dew condensation, and a low variance of obtained values, can be obtained.

To form the plurality of voids in the moisture sensing resistive substance, the fabric must be provided with a plurality of voids. To clarify the difference between the voids in the moisture sensing resistive substance and the voids in the fabric, the void in the fabric is referred to as "VOID" hereafter. As well known, the fabric has a greater or less or plurality of VOIDS and preferably VOID volume of the fabric to be used for manufacturing the moisture dew-detection sensor in accordance with the present invention is from 10% to 95%, more preferably from 30% to 85%.

The VOID volume of the fabric is determined from the following method, based on JIS L 1096-1979. Namely, three specimens having a size of 20 cm × 20 cm are prepared from the fabric, the weight thereof measured under a condition of 20° C. and 65% RH, respectively, and a weight per square m (W g/m$^2$) calculated from the obtained value. A mean thickness (t mm) of each specimen is obtained by measuring the thickness under a pressure of 125 g/cm$^2$ at five points of each specimen. An apparent specific gravity (S') of the fabric is calculated by the following equation $$S' = \frac{W}{1000 \times t}$$

A specific gravity (S) of a fiber constituting the fabric is measured at 4° C. by a picnometer.

The VOID volume (V.V) is calculated by the following equation $$V.V = \frac{S - S'}{S} \times 100$$

When the VOID volume is less than 10%, it is difficult to obtain a continuous void in the moisture sensing resistive substance, when adhering same to the fabric, and thus the response speed and the precision of measurement of the obtained moisture and dew-detection sensor are reduced. When the VOID volume is more than 95%, the mechanical strength of the obtained moisture and dew-detection sensor is too low and the reliability of a detected value is doubtful.

With regard to a fiber constituting the fabric, it is possible to use any type of fiber, as long as the influence of humidity on the fiber is low. For example, a synthetic fiber such as a polyester fiber, a polyacrylonitrile fiber, a polyamide fiber or the like, a glass fiber, a mineral fiber, a ceramic fiber or the like can be used.

A moisture sensing resistive substance will now be explained hereafter.

The moisture sensing resistive substance according to the present invention is one capable of changing an electrical resistance thereof by absorbing a moisture, and typically, is a hygroscopic high polymer in which a plurality of conductive particles are dispersed. When this substance absorbs a moisture, the high polymer in the substance swells and an electrical connection between adjacent conductive particles becomes unsatisfactory because the electrical resistance of the substance is increased.

A high polymer capable of forming in a substantially continuous film on a fabric or a fiber of the fabric, swelling in a hygroscopic state, and maintaining a configuration thereof even if the substance is swollen, can be used as the hygroscopic high polymer in the present invention. Preferably a hygroscopic high polymer having a water absorption of at least 20%, more preferably 100% or more under a condition of 25° C. and 65% RH, is used.

The water absorption of the high polymer can be obtained by the following method.

A moisture sensing resistive substance having a thickness of 100 μm and a size of 1 cm square is immersed in distilled water for 24 hrs. and the substance then placed on a screen of 100 mesh for 10 minutes under an atmosphere of 25° C. and 65% RH, and after removing water on a surface of the substance, the weight ($W_1$) of the substance is measured. The water absorption is calculated from the obtained value $W_1$ and the weight ($W_0$) of the original sample, i.e., not immersed substance, by the following equation.

$$\text{Water Absorption} = \frac{W_1}{W_0} \times 100(\%)$$

When the water absorption is less than 20%, a change of a value of the resistance of the moisture sensing resistive substance is small in the hygroscopic state, and a detected electrical signal is likely to be affected by noise, and thus this is not recommended.

A polyacrylamide, a polyvinylalcohol, a polyethylene oxide, a cellulose derivative high polymer such as a methyl cellulose, an ethyl cellulose or the like, a polyamide such as a nylon or the like, a polyvinyl pyrrolidone, a hygroscopic acrylate, a condensation polymer of an isobutylene and a maleic anhydride, a hygroscopic meta-acrylate, a polymer denatured therefrom, a composite polymer thereof or the like can be used as the nonionic hygroscopic high polymer.

When the moisture sensing resistive substance is prepared by mixing the conductive particles into the above nonionic hygroscopic high polymer, an electrical conduction in the substance is supplied by electronic conduction. Therefore, the moisture and dew-detection sensor produced by the substance including the nonionic hygroscopic high polymer can be operated by a direct electrical current, and thus a circuit having a simple constitution can be used as a circuit connected to the moisture and dew-detection sensor.

As the hygroscopic high polymer, a hygroscopic high polymer electrolyte such as a sodium polyacrylic acid or a mixture of the nonionic hygroscopic high polymer and an electrolyte can be used. Since the electrolyte has an ion conduction, it is possible to produce the moisture sensing resistive substance without the conductive particle. Of course, it is preferable to further add the conductive particles to the hygroscopic high polymer, but to prevent an influence of a change of the resistance caused by the ion conduction, it is preferable to use an alternating electric current.

Since the above high polymer per se can be adhered to the fiber, the moisture sensing resistic substance can be adhered to the fibers in the fabric without an additive. But, to improve the adhesion to the fiber in order to maintain a reliable serviceability in a dew state, it is preferable to apply a water nonsoluble treatment by providing a partial crosslinking to the high polymer by using a hydrophilic crosslinker or a crosslinked high polymer, or blending with another binding resin, e.g., an acrylic resin, urethane resin, epoxy resin, polyester resin, polyamide resin or the like, which have a good compatibility with the above high polymer and a strong adhesion to the fiber.

A carbon black can be usually used as the conductive particle dispersed in the hygroscopic high polymer. Further a carbon fiber, a conductive compound, a metal such as copper, nickel, silver, an alloy thereof or the like can be used as the conductive particle. To form a thin moisture sensing resistive substance and obtain good response characteristics, it is preferable to use particles having a smaller mean diameter than a diameter of fiber constituting the fabric. If an elongated substance, e.g., the fiber, is used as the conductive particle, a cut length of the fiber may be determined to be less than the diameter of the fiber constituting the fabric. Further, to uniformly disperse the conductive substance on a surface of the fiber, the mean diameter of the particle is preferably 1 $\mu$m or less.

A weight ratio between the conductive particles and the hygroscopic high polymer in the moisture sensing resistive substance is preferably determined as follows. Namely, 30 weight portion to 2500 weight portion of the conductive particles may be used to 100 weight portion of the hygroscopic high polymer. When the carbon black is used as the conductive particle, 30 weight portion to 400 weight portion of the carbon black, preferably 40 weight portion to 300 weight portion is used. When a content of the carbon black is greater than 400 weight portion, the adhesion of the moisture sensing resistive substance to the fiber becomes unsatisfactory, the mechanical strength of the moisture and dew-detection sensor is low, and a change of a value of resistance caused by the absorption of water is small. When the content of the carbon black is less than 30 weight portion, the electrical resistance of the moisture sensing resistive substance per se become too large, and thus is not preferable for practical use.

When from 30 wt portion to 200 wt portion of the carbon black is used in the moisture sensing resistive substance, it is possible to provide a moisture and dew-detection sensor capable of suddenly increasing a value of the resistance under a high humidity, as described in Examples 1 and 2 in detail hereafter, this sensor can be used as a moisture and dew-detection sensor for detecting a high humidity, and a generation and a dissolving of the dew condensation. When from 200 wt portion to 400 wt portion of carbon black is used in the moisture sensing resistive substance, it is possible to provide a moisture and dew-detection sensor having a value of resistance which can be gradually changed over a broad range of humidity, as described in an Example 5, and thus this sensor can be used as a moisture and dew-detection sensor for detecting humidity over a broad range.

A pick up of the moisture sensing resistive substance for a fabric in the moisture and dew-detection sensor in accordance with the present invention may be 10% o.w.f. to 100% o.w.f., preferably 30% o.w.f. to 90% o.w.f.

When the pick up is over 100% o.w.f., since a plurality of void in the sensor are filled by the moisture sensing resistive substance per se, it is impossible to obtain a sensor having a quick response speed and an accurate detection ability. When the pick up is less than 10% o.w.f., it is impossible to form the moisture sensing resistive substance in a continuous and uniformly dispersed state as a film on a surface of the fiber, so that a value of the resistance of the sensor becomes too large and it is impossible to obtain an accurate detection ability.

Further, it is more effective to provide a larger quantity of the moisture sensing resistive substance on a surface of the fabric. Such sensor can be obtained by applying a film of the moisture sensing resistive substance having a thinner thickness than that of the fabric, in a solution state, on the surface of the fabric by a transferring method.

The characteristics of changing a value of resistance thereof by a change of humidity in an environment to which the moisture and dew-detection sensor in accordance with the present invention is exposed, depends on the swelling characteristics of the hygroscopic high polymer and the content of conductive particles in the moisture sensing resistive substance.

A method of manufacturing the moisture and dew-detection sensor in accordance with the present invention will be described in detail hereafter.

First, a solution is prepared by dissolving the above-mentioned hygroscopic high polymer in a solvent such as water or an alcohol, and the above-mentioned conductive particles are dispersed in the solution. Next the obtained solution is applied to the above-mentioned fabric by an impregnating method or a coating method, and then the solvent is removed to obtain the moisture and dew-detection sensor. A dipping apparatus can be usually used for the impregnating method, and various coating devices such as a gravure roll, a kiss roll, a reverse roll or the like, and a transferring coating device, can be used for the coating method. The transferring coating is performed such that a coating medium is uniformly coated to a desired thickness on a sheet having good mold release characteristics, such as a mold release paper or the like, a fabric having a good liquid absorbing characteristics is plied on the sheet to ensure that the coating medium is impregnated in an absorbed state in the fabric, and finally the fabric with the coating medium is passed through a pair of rolls to uniformly disperse the coating medium in the fabric. This transferring coating is suitable when applying a solution of the moisture sensing resistive substance to a fabric composed of extra fine fibers and having a fine porous structure.

If all VOIDS of the fabric are filled with the moisture sensing resistive substance, a function of detecting the humidity and the generation or the dissolution of dew condensation in the moisture and dew-detection sensor is not obtained. Therefore, it is necessary to control the dispersion of the moisture sensing resistive substance in the fabric. This control can be performed by selecting a suitable concentration and quantity of the solution for the fabric used. The quantity of the solution in the fabric also can be controlled by arranging a pair of rolls downstream of a solution applying device and adjusting a pressure of the pair of rolls. In the latter case, since the fabric can recover the thickness thereof due to an inherent elasticity after squeezing the solution from the fabric by the pair of rolls, the plurality of voids can be easily provided in the moisture sensing resistive substance.

The characteristics of the sensor in accordance with the present invention are shown in FIGS. 3 to 7, and detailed explanations thereof will be given in the examples hereafter.

A moisture and dew-detection sensor device in accordance with the present invention will be now described in detail hereafter.

As shown in FIG. 1, the moisture and dew-detection sensor device comprises the above-mentioned moisture and dew-detection sensor 1, a pair of electrodes 2, conductive contacting portion 3 connecting the moisture and dew-detection sensor 1 to the electrode 2, respectively, and lead wires 4 attached to each electrode 2. Members holding and reinforcing each component constituting the device can be optionally used.

A known conductive paste, soldering paste, gripping device such as a conductive eyelet holder, conductive hook or the like can be used as the conductive contacting material 3.

When manufacturing the moisture and dew-detection sensor device capable of a highly sensitive detection of a change of humidity, the holding and reinforcing member should be as small as possible compared with an area of the moisture and dew-detection sensor, to maintain the high permeability of the sensor.

When manufacturing the moisture and dew-detection sensor device capable of detecting a generation of dew condensation, preferably the device is arranged as close as possible to a member to be detected, whereby a heat transfer from the member to be detected to the device is accelerated, to accurately detect a dew state of the material to be detected, with a rapid response speed.

Figure 8A:
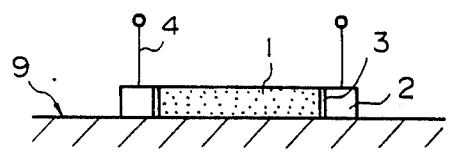
FIG. 8(a) to 8(c) are side views illustrating various states by which the moisture and dew-detection sensors are practically attached to a substance to be detected, respectively.
Figure 8B:
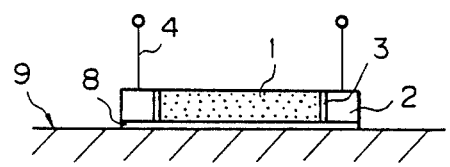
Figure 8C:
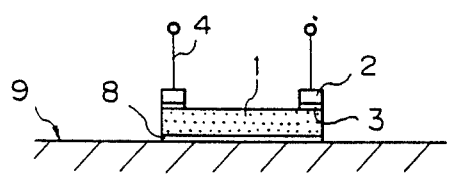

When the member to be detected is an insulating material such as a glass, a plastic or the like, as shown in FIG. 8(a), the sensor 1 may be directly adhered to a surface of the member to be detected, to directly adsorb or detect dew on the surface of the member to be detected. When the member to be detected is a conductive material such as a metal, it is preferable to provide a thin insulating layer 8 having a good thermal conductivity on a surface of the moisture and dew-detection sensor device opposing the member to be detected, as shown in FIG. 8(b), or use the moisture and dew-detection sensor on a opposing surface to be detected which is previously coated with the thin insulating layer 8 having a good thermal conductivity, before producing the moisture and dew-detection sensor device as shown in FIG. 8(c). In the latter case, since it is possible to make the insulating layer 8 thinner, the heat conductivity of the insulating layer becomes greater and a temperature of the sensor becomes the same as that of the member to be detected, so that when the dew condensation is generated on the member to be detected, the insulating layer 8 and the moisture and dew-detection sensor 1 are simultaneously subjected to the dew condensation. Note, in the latter case, the electrodes 2 are provided on a reverse surface of the surface coated with the insulating layer 8, as shown in FIG. 8(c).

Various materials, e.g., a plastic film, a plastic coating layer or the like, can be used as the thin insulating layer 8. Further when forming the thin insulating layer 8 as shown in FIG. 8(c), it is possible to apply the thin insulating layer by a spraying or transferring method.

As described hereinbefore, since the sensor 1 has a plurality of voids, all portions of the moisture sensing resistive substance 6 can be exposed to the atmosphere. Therefore, humidity or the generation of dew condensation can be quickly detected by the moisture sensing resistive substance having a large sensor surface, so that a response speed of the sensor when detecting humidity or the generation of dew condensation is increased. Further, when the device is attached to the member to be detected as shown in FIG. 8(a) to FIG. 8(c), since one side of the sensor, i.e., an upper side of the sensor in FIG. 8(a) to FIG. 8(c), is exposed to the atmosphere, a response speed of the sensor upon detecting the dissolving of the dew condensation also is increased.

The moisture and dew-detection sensor device in accordance with the present invention can be produced without a hard base plate such as a ceramic base plate, and the sensor itself is strong and flexible, and further, it is possible to select a thin and soft material as the insulating layer. Therefore, the device in accordance with the present invention can be closely attached to the member to be detected whether having a curve surface or an irregular surface.

Figure 9A:
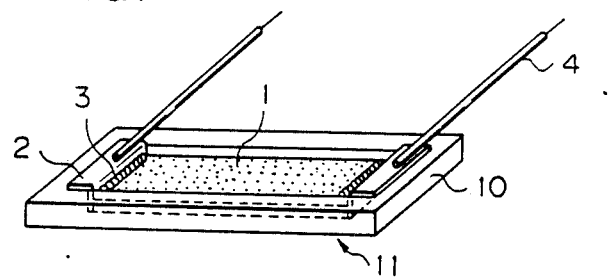
FIG. 9(a) to 9(c) are perspective views each illustrating an example of three type of the moisture and dew-detection sensor devices, respectively.
Figure 9B:
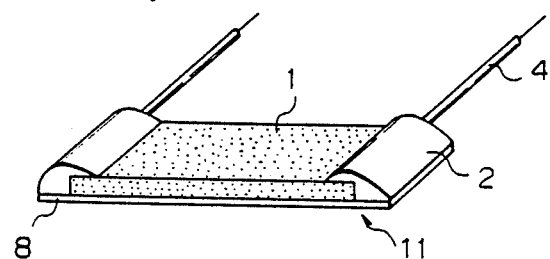

FIGS. 9(a)–9(b) show concrete examples of moisture and dew-detection sensor device using fundamental modes of attaching the device to the member to be detected illustrated in FIG. 8(a)-FIG. 8(c), respectively.

The device illustrated in FIG. 9(a) is one example of the device capable of directly absorbing dew condensation generated on the member to be detected, when the member to be detected is an insulating material as shown in FIG. 8(a). In this case, an insulating holder 10 made of a plate of an insulating material and having a frame shape is arranged to the moisture and dew-detection sensor such that an under surface of the moisture and dew-detection sensor coincides with an under surface of the insulating holder 10. Both inside ends at an upper side of the holder 10 are connected through conductive contacting portions 3 of a conductive adhesive or the like to electrodes 2 of a metal plate, respectively, and each leed wire 4 is connected to the electrodes 2 by solder, respectively.

The device illustrated in FIG. 9(b) is one of example of the device capable of detecting the generation or the dissolving of the dew condensation when the member to be detected is a conductive material as shown in FIG. 8(b). In this concrete example, an electrode 2 is formed by molding and curing a conductive adhesive in place of the metal electrode used in the concrete device shown in FIG. 9(a). At the time of molding the electrode 2, the moisture and dew-detection sensor 1 and the lead wire 4 are molten with the electrode 2. Therefore, in FIG. 9(b), a conductive contacting portion 3 is not indicated in the drawings. A very thin layer 8 of an insulating material is attached to a bottom surface of the device.

Figure 9C:
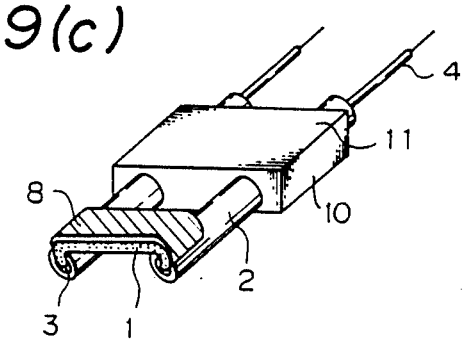

The device illustrated in FIG. 9(c) is another example of the device capable of detecting the generation or the dissolving of the dew condensation when the member to be detected is the conductive material as shown in FIG. 8(c). In this concrete device, an insulating holder 10 having a shape of a rectangular parallelopiped is used and two pin electrodes 2 having a tubular shape are penetrated in parallel into the insulating holder 10. One end of each of the two electrodes is attached to the moisture and dew-detection sensor 1 having an outside surface thinly coated with the insulating material 8 as shown in FIG. 9(c). In this case, preferably the sensor 1 and the holder 10 is assembled such that a surface of the insulating material 8 is in the same plane as a plane 11 contacting a member to be detected of the insulating holder 10. The other ends of the two electrodes 2 are connected to a lead wire 4, respectively. The moisture and dew-detection sensor device having the structure shown in FIG. 9(c) can be easily in a preciously contacting state mounted on the conductive member to be detected such as a metal.

When it is necessary to increase the strength of the moisture and dew-detection sensor, it is preferable to fix a plate having a good thermal conductivity, such as a metal plate, to the sensor by an insulating adhesive. Any type of metal or alloy having a good thermal conductivity can be used as the metal plate. But, from the viewpoint of easy handling, durability, strength, and cost, or the like, it is preferable to use an aluminium, stainless steel, copper, phosphor bronze, or duralumin plate or the like. A thickness of the metal plate is preferably thin, e.g., 2 mm or less, to effectively transfer a temperature of the member to the attached sensor device and to make the sensor device small. However, it is possible to produce another type of moisture and dew-detection sensor device capable of predicting an environment which is likely to generate dew condensation, by using a metal plate having a thicker thickness. Namely, since the metal plate having a thick thickness and a large area has large heat capacity, the metal plate itself is likely to generate dew condensation in a certain environment, so that the moisture and dew-detection sensor device having the thick metal plate can detect a state wherein the environment of the sensor device is likely to generate dew condensation.

Any type of material capable of adhering the sensor to the metal plate can be used as the insulating adhesive. For example, urethane, acrylic resin, epoxy resin or the like can be used. A thickness of an adhesive layer is preferably thin, to ensure no obstruction of a thermal conduction from the metal plate to the sensor, therefore it is preferable to apply a thin adhesive layer capable of maintaining an insulating property of the adhesive layer by a coating treatment or the like. Further to improve a thermal conductivity of the adhesive layer, a metal powder, a glass powder, a ceramic powder or the like may be mixed with the adhesive, while maintaining the insulating property thereof.

As described hereinbefore, the insulating holder may be used for manufacturing the moisture and dew-detection sensor device from the moisture and dew-detection sensor, the electrodes, the lead wires or the like.

Figures 10A, 10B:
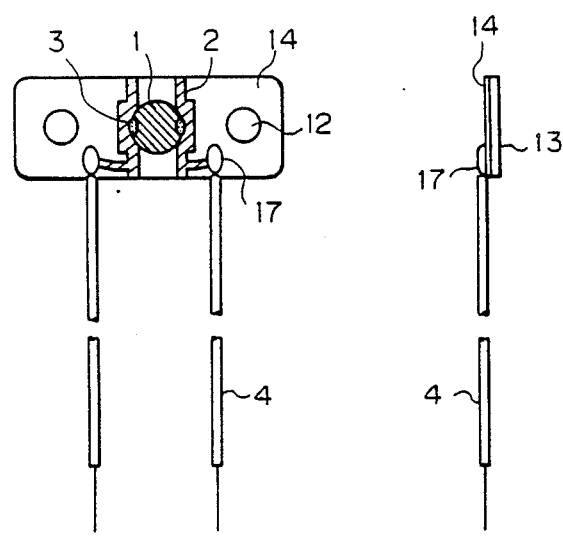
Figure 10C:
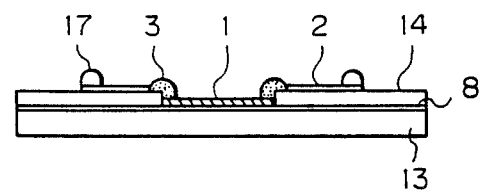

An example of a moisture and dew-detection sensor device including an insulating holder and a metal plate is illustrated in FIG. 10(a), FIG. 10(b), and FIG. 10(c). FIG. 10(a) is a front view, FIG. 10(b) is a side view, and FIG. 10(c) is a cross sectional view. A shape of the sensor device shown in FIG. 10(A) to FIG. 10(C) is similar to that of a conventional sensor device using a ceramic sensor.

In the drawings, numeral 1 is a moisture and dew-detection sensor composed of a nonwoven fabric constituted by a plurality of fibers having a diameter of 5 $\mu$m or less and a moisture sensing resistive substance dispersed in the nonwoven fabric, 2 an electrode, 3 a conductive contacting portion, 4 a lead wire connected to the electrode 2 by a solder 17, 8 an insulating adhesive layer for adhering the moisture and dew-detection sensor 1, or a holder 14 of an insulating material, to a metal plate 13, and 12 denotes holes to be used to attach the sensor device to a substance to be detected, by screws (not shown).

In this sensor device, since the sensor 1 includes a plurality of fine voids, moisture in the atmosphere can be travel through the plurality of fine voids and reach a surface of the insulating adhesive layer, and the humidity and the generation or dissolving of the dew condensation can be detected by the entire sensor 1.

This sensor device is used by directly attaching the metal plate 13 to a surface of a substance to be detected. In this case, since a heat conductivity of the metal plate is good, the generation or the dissolving of the dew condensation on a surface opposite to the sensor 1 of the insulating adhesive layer 8 correctly responds to the generation or the dissolving of the dew condensation on a substance to be detected.

A preferable example of a moisture and dew-detection sensor device is illustrated in FIG. 11(a) and FIG. 11(b). FIG. 11(a) is a front view and FIG. 11(b) is a side view. As can be easily understood when comparing FIG. 11(b) with FIG. 10(c), the holder 14 of an insulating material is not used in this sensor device. Namely in this sensor device, an aluminium printed circuit board 13 to which a sensor 1 is attached by conductive contacting portions 3 of a conductive paste is used. The electrode circuit 2 is formed by etching a copper leaf on the aluminium printed circuit board 13. In the drawings, 4 denotes a lead wire, 8 an insulating adhesive layer, 16 a connector connecting the lead wire 4 to a detecting circuit, and 17 a portion in which the electrode circuit 2 is connected to the lead wire 4 by a solder.

Use of the aluminium printed circuit board provides the following features.

(1) The electrode circuit can be easily provided on a desired portion by etching.

(2) A surface of the aluminum printed circuit board from which copper is removed by the etching process becomes an insulating adhesive layer having a good heat conductivity, and thus it is not necessary to provide another insulating layer.

(3) Since aluminium is used, the heat conductivity is good.

(4) Since aluminium has a good workability, it is easily to form the sensor device into a shape corresponding to a shape of a substance to be detected and to provide a hole to be used when attaching the sensor device to the substance to be detected.

When using a plate-like member having a good heat conductivity, with the moisture and dew-detection sensor, it is necessary to attach the plate-like member to a substance to be detected without causing a heat loss between the plate like member and the substance to be detected Accordingly, it is necessary to increase a degree of adhesion between both substances, to use as thin as possible an adhesive, or to select an adhesive having a good heat conductivity. As the adhesive having a good heat conductivity, a conductive adhesive such as a conductive paste, an anisotropic adhesive, an adhesive mixed with a ceramic powder having a good heat conductivity, a silicon group adhesive or an epoxy group adhesive, can be used. Further, when a thin and flexible material is used as the holder supporting the sensor device and/or a metal plate attached to the holder, even if the substance to be detected has a curved surface or an irregular surface, the sensor device can be fixed with a good adhesion to the substance to be detected If necessary, it is possible to attach the sensor device to the substance to be detected by inserting a screw into a hole arranged on the holder (see hole 12 in FIG. 10(A)).

When it is necessary to prevent a direct impingement of dew or an oil-mist on the moisture and dew-detection sensor, it is preferable to use a fabric such as a mesh, a woven fabric, a knitted fabric or a nonwoven fabric, having an air permeability and a resistance to water and oil, as a cover. The resistance to water and oil of the fabric can be obtained by immersing the fabric in a fluoro group water and oil repellent, and curing the fabric.

Figure 12A:
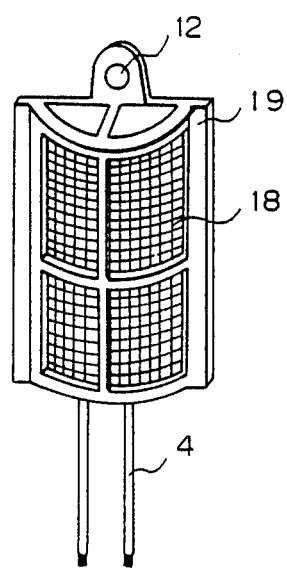
Figure 12B:
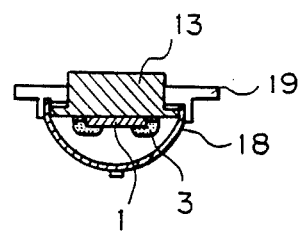

FIG. 12(A) and FIG. 12(B) show an example of the moisture and dew-detection sensor device. In this example, a plastic case 19 having a fabric 18 is used, and the sensor device is arranged in the plastic case 19. In the drawing, 1 denotes a moisture and dew-detection sensor, 3 a conductive contacting material, 12 a hole, and 13 a conductive plate-like material. The moisture and dew-detection sensor device in accordance with the present invention can be used in a poor environment such as a kitchen or a bath room, where water or an oil-mist can impinge directly on the sensor device, by providing the above-mentioned cover. A fabric having air permeability and a resistance to water and oil can be obtained, for example, by applying the fluoro group water and oil repellent "Asahiguard AG750", supplied by Meisei Kagaku Co., to a polyester mesh fabric having a 250 mesh, and curing same at a temperature of 150° C.

A moisture and dew-detection sensor module in accordance with the present invention will be now described in detail.

Figure 13A:
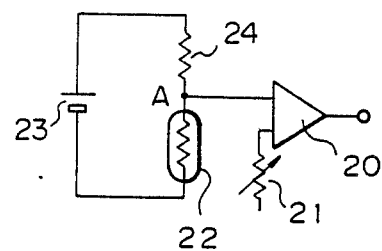
FIG. 13(a) is a view illustrating an example of a digital output circuit capable of outputting a change of a value of resistance in the moisture and dew-detection sensor device in accordance with the present invention as a digital electric voltage or a digital electric current.

In the present application, a unit in which the moisture and dew-detection sensor device is combined with a detecting circuit capable of outputting a change of a value of a resistance of the moisture and dew-detection sensor as a signal of an electric voltage or an electric current is called a moisture and dew-detection sensor module. A conventional detecting circuit may be used as the above-mentioned detecting circuit. An example of the detecting circuit is illustrated in FIG. 13(a). In this detection device, a resistance 24 is connected in series to the sensor 22, and an electric potential in a position A between the sensor 22 and the resistance 24 is compared at a comparator 20 with an electric potential predetermined by a rheostat 21. When the electric potential in the position A exceeds a predetermined electric potential, the detecting circuit outputs a digital signal of the electric voltage on the electric current. In the drawing, 23 is a power supply.

Figure 13B:
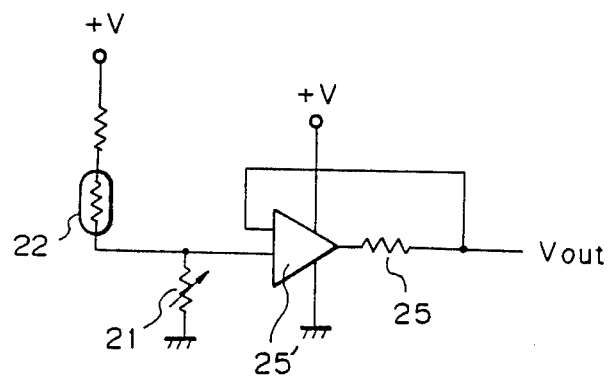
FIG. 13(b) is a view illustrating an example of an analog output circuit.

Another example of the detecting circuit is illustrated in FIG. 13(b). This detecting circuit outputs an analog signal of the electric voltage of the electric current. In the drawing, 21 is a rheostat, 25 a resistance, and 25, an analog IC.

The moisture and dew-detection sensor module may further include a connecting device in which the detecting circuit, a relay activated by the signal output from the detecting circuit and switching a main power supply, and a terminal connected to the main power supply.

Figure 14:
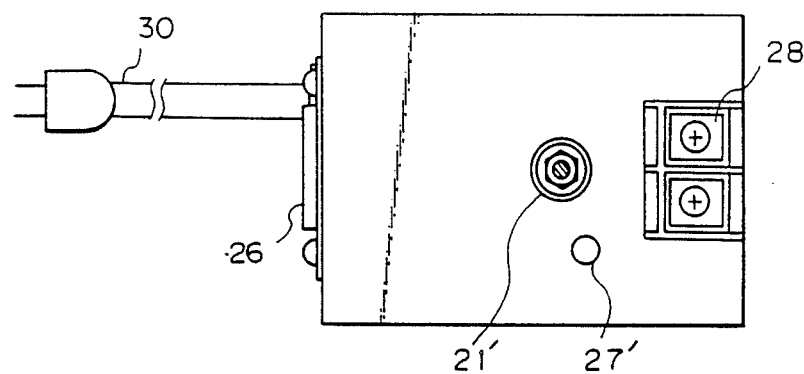
FIG. 14 is a view illustrating a connecting device for connecting the moisture and dew-detection sensor device to an electric source.
Figure 15:
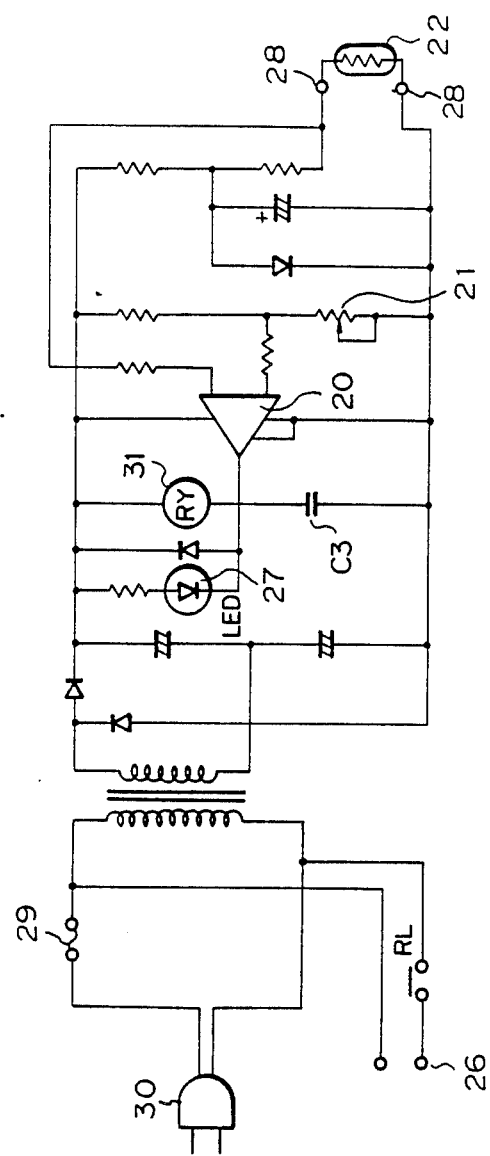
FIG. 15 is a view illustrating a circuit of the connecting device illustrated in FIG. 14.

An example of the moisture and dew-detection sensor module is illustrated in FIGS. 14 and 15. The appearance of the moisture and dew-detection sensor module is illustrated, in FIG. 14, and an electric circuit in the moisture and dew-detection sensor module is illustrated in FIG. 15. In the drawings, 20 denotes a comparator, 21 a rheostat, 21, a knob for adjusting the rheostat 21, 22 a sensor device, 26 a terminal outputting AC 100 V, 27 a light emitting diode, 27' an LED indicating unit including the light emitting diode 27, 28 a connecting terminal of the sensor device, 29 a fuse, 30 an outlet, and 31 a relay. As it is possible to use an AC 100 V electrical power for the above connecting device, the moisture and dew-detection sensor can be commonly used to operate an outside device, e.g., a heater or the like, by the above connecting device.

Figure 16:
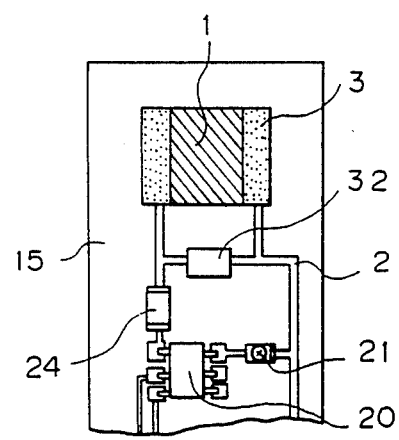
FIG. 16 is a view illustrating an example of a moisture and dew-detection sensor module in accordance with the present invention and including the moisture and dew-detection sensor and a detecting circuit.

Another example of the moisture and dew-detection sensor module is illustrated in FIG. 16. In this sensor module, the detecting circuit is mounted on a printed circuit board with the moisture and dew-detection sensor device. In the drawing, 1 denotes a moisture and dew-detection sensor, 2 an electrode circuit, 3 a conductive contacting portion, 15 a printed circuit board, 20 a comparator, 21 a rheostat, and 24 a resistance. A polyimide flexible printed circuit board or an aluminum printed circuit board having a thickness or 25 μm or less, respectively, can be used as the printed circuit board having a good heat conductivity. A power source terminal and an output terminal (not illustrated in FIG. 16) are arranged in the sensor module. A large amount of water is present on the surface of the printed circuit board when dew condensation is generated, and therefore it is necessary to embed all circuits of the sensor module in a silicon resin or an epoxy resin. Since the sensor module illustrated in FIG. 16 is made in a compact shape of a plate-like material, including the sensor device and the detecting circuit, this sensor module can be assembled with other printed circuit boards constituting each element of an apparatus such as a measuring device, a computer or the like, in which the prevention of a high humidity in a housing of the apparatus is necessary. Further this sensor device is able to be used in assembly line of the apparatus.

The moisture and dew-detection sensor device and the moisture and dew-detection sensor module in accordance with the present invention can be used for the following applications. Namely, the sensor device or the sensor module can be used as a humidity sensor for a room air conditioner, a dehumidifier, a duplicator or the like, and as a humidity control device of a room for storing paintings or experimental equipment or the like. Further the sensor device or the sensor module in accordance with the present invention can be used as a dew condensation detecting sensor capable of rapidly detecting a high humidity upon a generation of dew condensation.

In the present application, a system including the moisture and dew-detection sensor module and a device capable of emitting an alarm such as a sound or a light, or operating a heater, a ventilation fan, a heater fan, a dehumidifier or the like is called a moisture and dew-detection sensor system.

The applications of the moisture and dew-detection sensor system in accordance with the present invention are as follows:

(1) A system operating a lock mechanism or an apparatus for dissolving a dew condensation to prevent a roll-in of a magnetic tape caused by a generation of dew condensation in a magnetic head of a magnetic recording and replaying apparatus such as a portable tape recorder, a portable video tape recorder, a computer or the like.

(2) A system operating a dehumidifying fan or a heater when humidity in an environment becomes too high, to prevent the generation of dew condensation on a lens such as a camera lens, a collecting lens for a laser dish and a facsimile machine, a photo sensor, a lens in an infrared ray detector or the like.

(3) A system for detecting and preventing dew condensation generated on a north wall of a room, a system for removing dew condensation generated on an aluminum sash, a dew condensation alarm system for detecting excess water which cannot be absorbed by a water absorption sheet and warning of the need to change the water absorption sheet, a system for automatically switching on a ventilator fan in a kitchen or a bath room, a system for automatically switching on a fan capable of preventing decay of a portion of a pillar under a floor, a system for demisting a mirror of a washstand, a system for preventing a generation of dew condensation on stock in a warehouse, a system for preventing a generation of dew condensation on goods in a truck or a ship, a system for warning of a misting of a glass of a showwindow or an automobile, estimating a time at which a dew condensation is generated and preventing a generation of the dew condensation, and a system for preventing a misting of a reflecting mirror arranged on a road.

(4) A system for detecting in advance a generation of dew condensation in a production line such as for steel manufacturing equipment, a system for detecting a leakage of water and warning of such a leakage, a system for detecting in advance a generation of dew condensation in a metal mold and a system for detecting and preventing a generation of dew condensation in a switchboard.

(5) A system for warning of an approach of rain and moving washing from outside to under cover, a system for closing a window and a system for determining a degree of drying of a washing arranged outside.

Typical applications among the above various application will be now described.

Figure 17A:
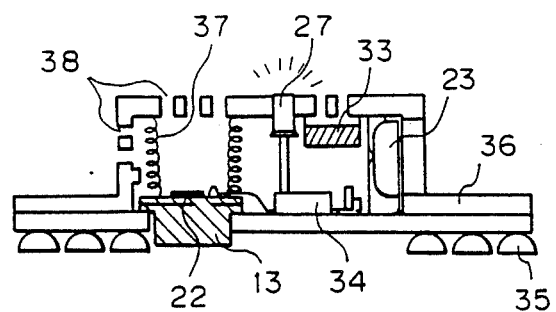
Figure 17B:
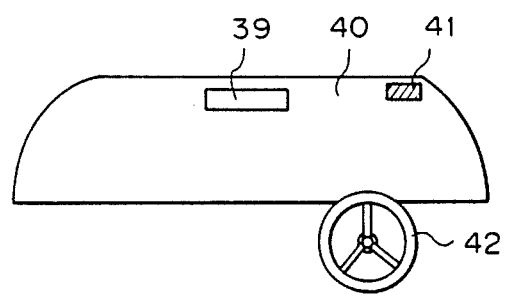

A system for warning in advance of a starting time of a misting of a front glass of a automobile, by sound and light, is illustrated in FIG. 17(a) and FIG. 17(b). FIG. 17(a) is a view explaining a mounting state of the system near to the front glass and FIG. 17(b) is a plan view illustrating the mounting position of the system. In the drawings, 12 denotes a metal plate having a good heat conductivity, 22 a moisture and dew-detection sensor, 23 a cell, 27 a luminous diode, 33 a buzzer, 34 a detecting circuit housing, 35 a sucker type attaching element capable of easily mounting and dismounting the system to a front glass 40, 36 a housing for accommodating the system, 37 a spring for pressing the sensor onto the front glass, 38 a hole through which air can pass, 39 a room mirror of the automobile, 41 a position where the system is mounted, and 42 a steering wheel.

Since air in a cabin of the automobile can freely pass through the holes 38 to a place near to the sensor 22, a high humidity state of the air near to the front glass caused by a lowering of a temperature of the front glass can be accurately detected by the sensor, and thus it is possible to know in advance of the generation of misting. The system can be attached to a more suitable place for detecting the humidity by the sucker type attaching element.

Figure 18:
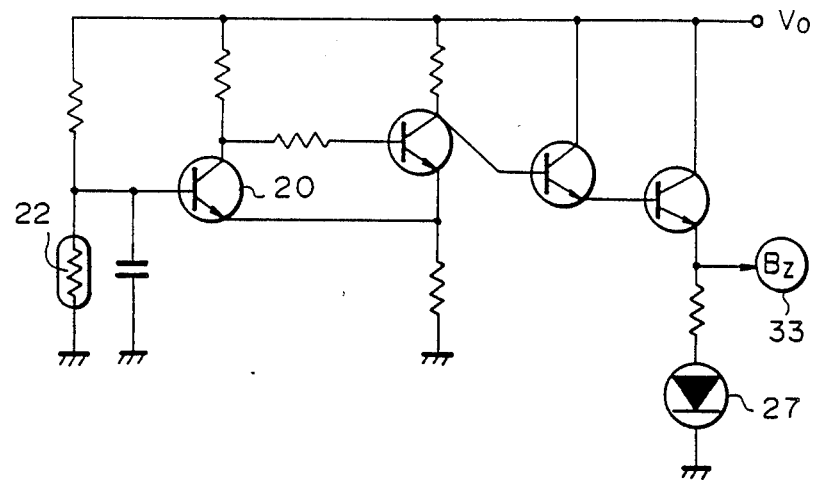
FIG. 18 is a view illustrating a circuit used in the apparatus in FIG. 17.

FIG. 18 illustrates an example of a circuit used in the system illustrated in FIG. 17(a) and FIG. 17(b). In the drawing, 20 denotes a comparator, 22 a sensor, 27 a luminous diode, and 33 a buzzer.

Figure 19:
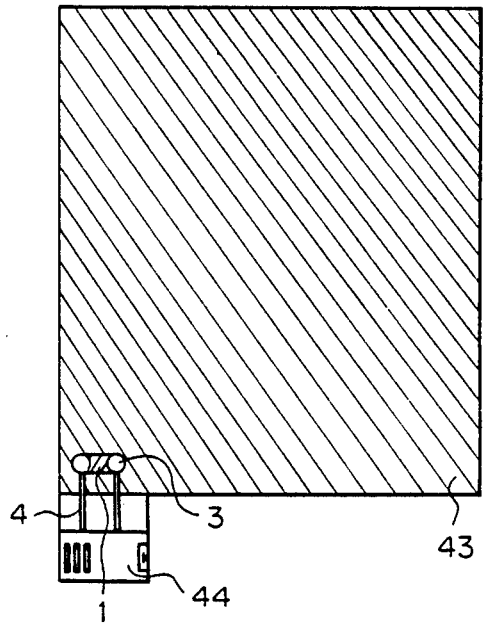
FIG. 19 is a view illustrating the moisture and dew-detection sensor system applied to a dew preventing and water absorbing sheet.

A dew condensation alarm system for detecting excess water which cannot be absorbed by a water absorption sheet arranged on a north wall of a room and warning that an exchange of the water absorption sheet is necessary, is illustrated in FIG. 19. A sensor 1 is attached to the water absorption sheet 43 by a pair of metal snap hooks 3 operating as electrodes. When an absorption ability of the water absorption sheet is saturated and excess water appears on a surface of the water absorption sheet, the system detects the excess water and an alarm 44, i.e., a buzzer, is operated to warn that the water absorption sheet must be changed. To prevent wastage of a cell caused by a continuous operation of the buzzer when the room is unattended, it is preferable to build in a timer capable, for example, of operating for one minute every one hour in the system.

A nonwoven sheet manufactured by blending an absorption fiber of a copolymer of a polyacrylonitrile and an acrylic soda with an acrylic fiber can be used as the water absorption sheet.

Figure 20:
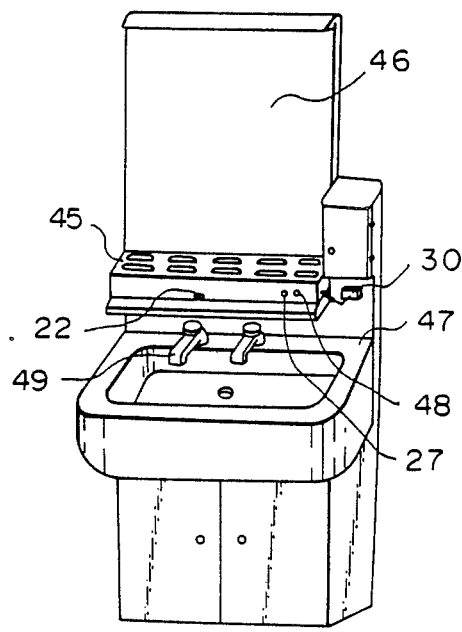
FIG. 20 is a view illustrating another example of a moisture and dew-detection sensor system, i.e., a demister for a mirror of a washstand.

A system for demisting a mirror of a washstand is illustrated in FIG. 20. A dehumidifier 45 including a sensor device 22 and a bar-like heater fan (not shown) is arranged on a shelf of the washstand. When the sensor device 22 detects that the humidity of the environment exceeds a predetermined value, the sensor device 22 operates the heater fan to demist the mirror 46. In the drawing, 27 is a luminous diode, 30 an outlet, 47 a wash bowl, 48 a switch, and 49 a faucet. It is possible to use a method for adhering an apparent film including a pyrogenic resistance on the glass, to demist the glass.

Figure 21A:
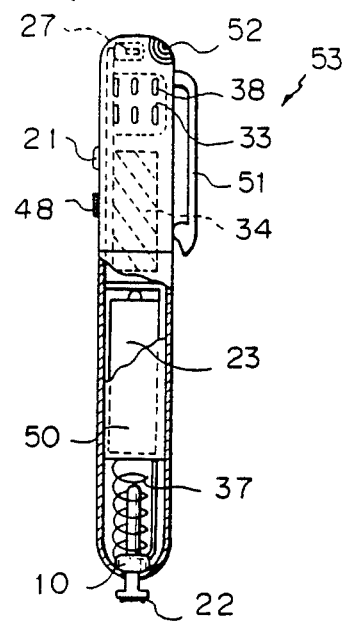
Figure 21B:
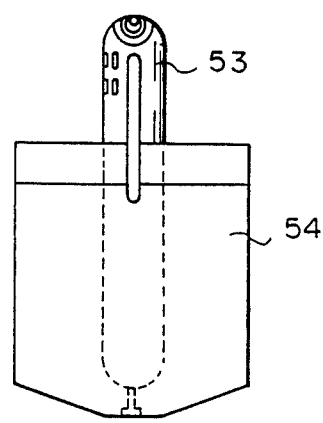

A pen type drying information system is illustrated in FIG. 21(a) and FIG. 21(b). FIG. 21(a) is a cross sectional view of the system, and FIG. 21(b) is a view explaining the use of the system in a pocket. As illustrated in FIG. 21(a), all elements constituting the system are contained in a housing having a shape similar to that of a pen.

A holder 10 having a sensor device 22 on a top thereof is urged toward the outside by a spring 37 to ensure that the sensor device 22 is improper contact with a bottom of a pocket 54. In the drawing, 21 is a dial for adjusting a rheostat, 23 a cell, 27 a luminous diode, 33 a buzzer, 34 a detecting circuit, 38 openings for the buzzer 33, 48 a switch, 50 a cell housing, and 52 a window for the luminous diode. When washing is being dried and the water content of the washing falls below a predetermined value, the system is operated and the state of the washing is denoted by a sound or a light. This system may be applied to a clothes pin type housing.

Although the moisture and dew-detection sensor, the moisture and dew-detection sensor device, the moisture and dew-detection sensor module and the moisture and dew-detection sensor system are described with reference to the attached drawings, the present inventions is not limited by examples described on the basis of the drawings, and the present invention can be applied to various application within the scope of the claims appended hereto.

EXAMPLES

The present invention will be further explained by means of examples, which in no way limit the invention. The definitions and measurements of various characteristics, used in these examples, are as follows.

Response Time upon Generation of Dew Condensation

Interval between a time at which a value of a resistance of a sensor is increased and a time at which the resistance value reaches a constant value, when a sensor device attached to a stainless steel plate having a thickness of 5 mm and 5 cm square by screws and held in an environment of 0° C. is placed in an environment under a temperature of 25° C. and a relative humidity of 80%.

Dew Condensation Accuracy

Difference between a time at which an increase of a value of resistance of a sensor occur and a time at which generation of a dew condensation on a substance to be detected or a plate supporting the sensor actually begins.

Response Time at Dissolution of Dew Condensation

Interval between a time at which a decrease of a value of resistance of a sensor occurs and a time at which the value of the resistance returns to the original value before dew condensation, when a sensor device is maintained in an environment under a temperature of 25° C. and a relative humidity of 80%, to naturally dissolve the dew condensation.

Dew Dissolution Accuracy

Difference between a time at which a decrease of a value of resistance of a sensor occurs and a time at which dissolution of a dew condensation on a substance to be detected or a plate supporting the sensor actually begins.

Measurement of Resistance of Moisture or Dew-detection Sensor Device under Various Relative Humidity Conditions A measurement of a resistance of a moisture and dew-detection sensor device is performed in a thermo and humidistate supplied by Masuda Rika Kogyo Co., Ltd., at 25° C. by changing a humidity in 5% increments from 0% to 100%, and then by changing the humidity in 5% increments from 100% to 0%. A digital Multimeter supplied by Advantech Co., Ltd., is used for the measurement of the resistance, and the measurement is performed after an environment in the thermo and humidistat reaches set humidity by keeping for five minutes after an indicator of the thermo and humidistat indicates the set humidity.

EXAMPLE 1

Figure 22:
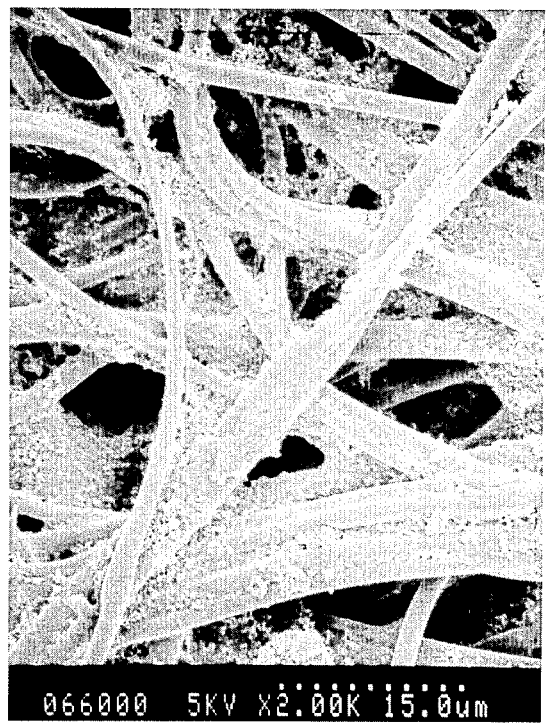
FIG. 22 is a electron micrograph illustrating a constitution of a moisture and dew-detection sensor in accordance with the present invention.

A polyvinyl alcohol of 100 wt portion, particles having a mean diameter of about 30 nm of a conductive carbon black of 80 wt portion, an acrylic resin of 70 wt portion and an urea formalin condensate of 2 wt portion which is used to partially cross link the polyvinyl alcohol, are blended, and the blended material is mixed with water of 1200 wt portion to form a paste of a moisture sensing resistive substance. A water absorption at 25° C. and 65% RH of a film of the moisture sensing resistive substance is 1500%. A nonwoven fabric having a VOID ratio of 60% and a weight per unit area of 15 g/m$^2$ is manufactured from an extra fine polyethylene terephthalate having a mean diameter of 1.7 μM, by a melt blow method. The nonwoven fabric is coated with the moisture sensing resistive substance by transfer coating, is dried at 60° C., and then is cured at 150° C. for 10 minutes. A thickness of the obtained sheet is 48 μm, and a pick up of the moisture sensing resistive substance in the obtained sheet is 60% o.w.f. A rectangular sensor having a length of 4 mm and a width of 2 mm is cut from the obtained sheet. An electron micrograph illustrating a constitution of this sensor is illustrated in FIG. 22. Both ends of the sensor are connected through a conductive adhesive to electrodes, the two electrodes are connected to a lead wire, respectively, and the sensor is mounted in a holder of a polyethylene to provide a sample I of a moisture and dew-detection sensor device having a constitution illustrated in FIG. 9(a).

To prepare a sample II of a moisture and dew-detection sensor device having a constitution illustrated in FIG. 9(b), the same moisture and dew-detection sensor as used in sample 1 is piled on a film of a polyethylene terephthalate and has a thickness of 4 μm, a length of 5 mm, and a width of 2.5 mm. Both ends of the obtained sensor are attached to electrodes by moulding and curing a conductive adhesive, respectively, and a lead wire is embedded in the electrode, respectively.

Samples III to V of a sensor device are prepared by using the same manufacturing method as that used for sample I, except that a different type of a nonwoven fabric is used, respectively. Namely, sample III of the sensor device uses a nonwoven fabric having a VOID ratio of 55% and manufactured from a polyethylene terephthalate fiber having a mean diameter of 8.0 μm by a spunbord method. A spunbord nonwoven fabric used in sample IV of the sensor device has a VOID ratio of 48% and is manufactured from a polyethylene terephthalate fiber having a mean diameter of 27.0 μm, and a spunbord nonwoven fabric used in sample V has a VOID ratio of 30% and is manufactured from a polyethylene terephthalate having a mean diameter of 35.0 μm.

Sample VI of a sensor device is prepared by using the same manufacturing method as used for sample II, except that a polyester woven fabric is used in place of the nonwoven fabric used in sample II. The polyester woven fabric is prepared by weaving warp yarns of a polyethylene terephthalate filament of 50 d/45 filament, and diameter of a single filament being 27 μm, and weft yarns of a polyethylene terephthalate filament of 75 d/36 filament and having the same diameter of the single filament as the warp yarn, into a plain weave and by solubilizing the filament at 100° C. in a solution of sodium hydroxide of 80 g/l, to reduce a weight of the fabric by 20%. A VOID rate of the obtained fabric is 16%.

Figure 3:
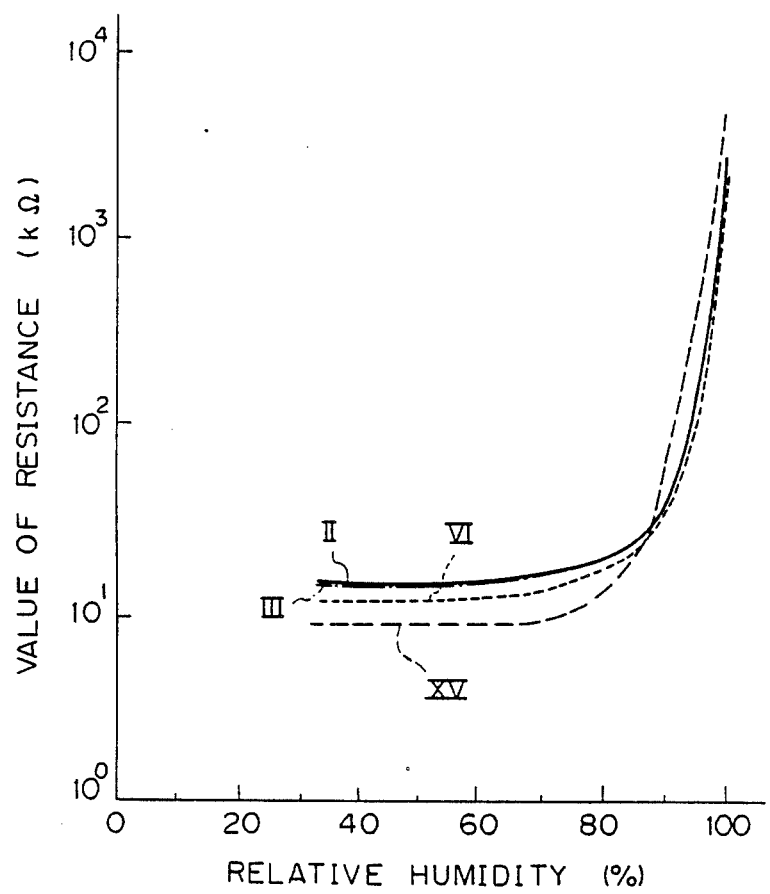
FIG. 3 is a graph illustrating changes of a value of resistance of four samples of the moisture and dew-detection sensors in accordance with the present invention against values of relative humidity in an atmosphere to which the moisture and dew-detection sensor is exposed.
Figure 4:
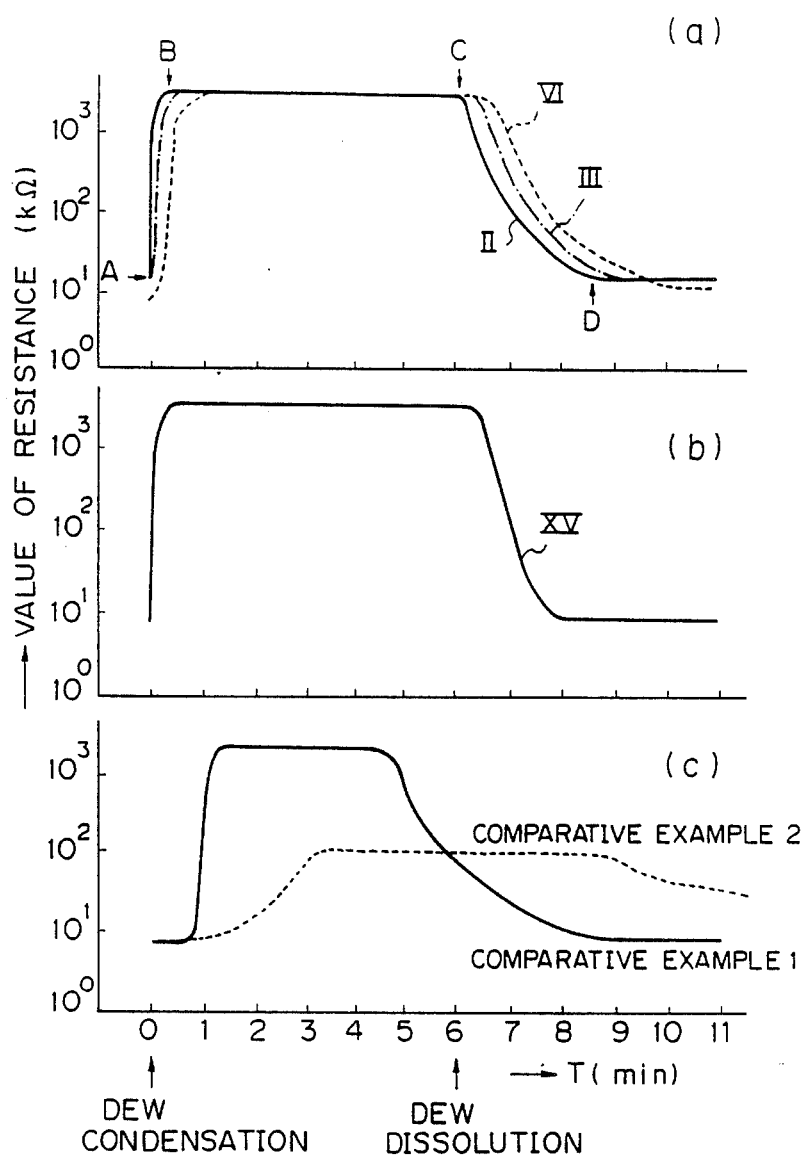
FIG. 4 is a graph illustrating time-dependent changes of a value of resistance of four samples of the moisture and dew-detection sensors in accordance with the present invention and two comparative example.

Values of the resistance before and after a generation of dew condensation, response times at the generation and dissolution of the dew condensation, and dew condensation accuracies thereof for samples I to VI were measured, and are shown in Table 1. Further changes of a value of resistance for samples I, III and VI under various relative humidity conditions are illustrated in FIG. 3, and changes of the resistance with time for samples II, III and VI are illustrated in FIG. 4(a). From the Table 1, FIG. 3 and FIG. 4(a), the following features of the sensor device in accordance with the present invention are clarified.

(1) With regard to the response time and the dew condensation, a sensor device prepared with a nonwoven fabric has a better value than that of a sensor device prepared with a woven fabric, and a sensor device prepared with a nonwoven fabric composed of fibers having a small diameter has a better value than that of a sensor device prepared with a nonwoven fabric composed of fibers having a large diameter. The resistances of the sensor devices in accordance with the present invention changes suddenly in a region higher than a relative humidity of 90% or more.

EXAMPLE 2

A polyacrylamide of 100 wt portion, particles having a mean diameter of about 30 nm of a conductive carbon black of 120 wt portion, an acrylic binder resin of 50 wt portion and a formalin of 3 wt portion which is used to partially cross link the polyacrylamide, are blended, and the blended material is mixed with water of 800 wt portion to form a paste of a moisture sensing resistive substance. A water absorption at 25° C. and 65% RH of a film of the moisture sensing resistive substance is 1300%. A nonwoven fabric having a VOID ratio of 50% and a weight per unit area of 20 g/m$^2$ is manufactured from an extra fine glass fiber having a mean diameter of 2 μm by a paper making method. The nonwoven fabric is immersed in the paste of the moisture sensing resistive substance, is dried at 60° C., and then cured at 150° C. for 10 minutes. A thickness of the obtained sheet is 40 μm, and a pick up of the moisture sensing resistive substance in the obtained sheet is 55% o.w.f. A semi-cured film of a polyurethane is adhered to the obtained sheet and is cured at 130° C. to form an thin insulating layer having a thickness of 7 μm. A rectangular sensor having a length of 5 mm and a width of 2 mm is cut from the obtained sheet.

A sample VX of a moisture and dew-detection sensor device in accordance with the present invention and having a constitution illustrated in FIG. 9(c) is manufactured from the obtained sheet.

Values of a resistance before and after a generation of dew condensation, response times at the generation and a dissolution of the dew condensation, and dew condensation accuracies thereof for sample XV were measured, and are shown in Table 1. Further a change of a value of resistance of sample XV under various relative humidity conditions is illustrated in FIG. 3, and a change of the resistance with time of sample No. XV is illustrated in FIG. 4(b).

A time for a detection of the dew condensation, i.e., the response speed, is fast, i.e., about 20 sec, and the dew condensation accuracies of the generation and the dissolution of the dew condensation are also fast, i.e, within 1 sec. The resistance of sample No. XV is 9.5 kΩ in a dry state and 2.6 MΩ in a dew state.

Ten sensor devices having the constitution of sample No. XV were prepared, and the resistances of each of the ten sensor devices were measured. Variations of the resistances of the ten sensor devices are between 15% and −15%, and the variations of the other characteristics are also small.

EXAMPLE 3

A polyacrylamide of 100 wt portion, particles having a mean diameter of about 30 nm of a conductive carbon black of 100 wt portion, an acrylic binder resin of 65 wt portion and a formalin of 3 wt portion which is used to partially cross link the polyacrylamide, are blended, and the blended materials are mixed with water of 100 wt portion to form a paste of a moisture sensing resistive substance. A water absorption at 25° C. and 65% RH of a film of the moisture sensing refractive substance is 1000%. A nonwoven fabric having a VOID ratio of 50% and a weight per unit area of 20 g/m$^2$ is manufactured from an extra fine glass fiber having a mean diameter of 2 μm by a paper making method. The nonwoven fabric is immersed in the paste of the moisture sensing resistive substance, dried at 60° C., and cured at 150° C. for 10 minutes. In this case, to prepare six samples of the sensor devices in accordance with the present invention, the concentration of the paste is diluted with water so that a pick up of the moisture sensing resistive substance on the nonwoven fabric becomes 5% o.w.f., 15% o.w.f., 35% o.w.f., 55% o.w.f., 95% o.w.f., and 120% o.w.f. The obtained six sheets are cut to form a circular sensor having a diameter of 30 mmφ, respectively. And these sensors are adhered through an acrylic adhesive layer to a center of an aluminium plate having a thickness of 0.5 mm, a length of 16 mm, a width of 6 mm, and a thermal conductivity of 0.52 cal/cm.s.k. To obtain six samples of the sensor device having a constitution illustrated in FIG. 10(a) to FIG. 10(c), i.e., samples VII to XII, insulating members of an ebonite reinforced with glass fibers, electrode and lead wires are used.

Resistance values before and after a generation of a dew condensation, response times at the generation and dissolution of the dew condensation, and dew condensation accuracies thereof for the six samples VIII to XII of the sensor device were measured, and are shown in Table 1. Further changes of the resistance under various relative humidity condition value for sample X, in which the pick up of the moisture sensing resistive substance is 55% o.w.f., and sample XI in which the pick up of the moisture sensing resistive substance is 93% o.w.f., are illustrated in FIG. 6, and changes of the resistance with time for samples X and XI are illustrated in FIG. 7(a) and FIG. 7(b).

Figure 6:
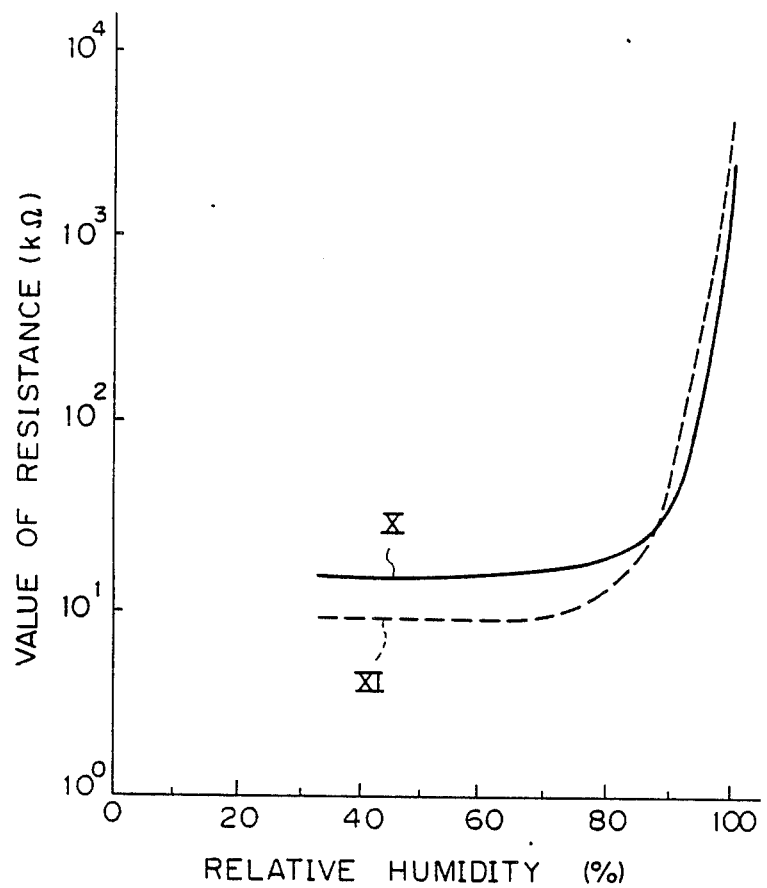
FIG. 6 is the same graph of two other samples of the moisture and dew-detection sensors in accordance with the present invention as that illustrated in FIGS. 3 and 5.
Figure 7:
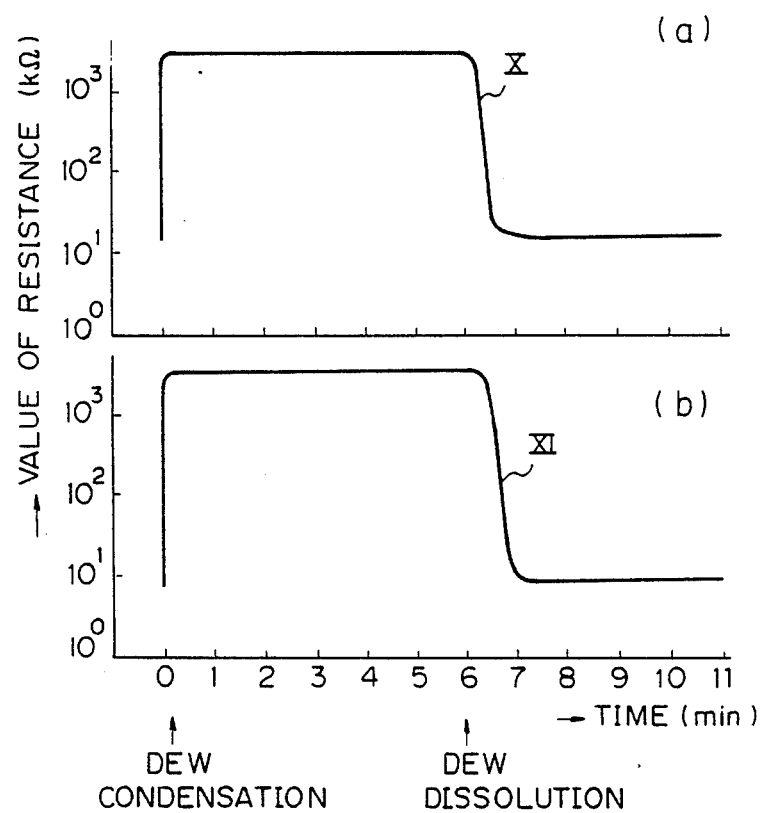
FIG. 7 is the same graph of two other samples of the moisture and dew-detection sensor in accordance with the present invention as that illustrated in FIG. 4.

As can be seen from FIG. 6, since the resistance of samples X and XI increases suddenly in a range of the humidity of over 90%, the above samples are excellent sensor devices.

With regard to the pick up, the response time and the dew condensation accuracy are lowered when the pick up is increased, due to a decrease in the voids in the moisture sensing resistive substance caused by the increase of the pick up. However, when the pick up is too small, the resistance becomes unpractically large.

EXAMPLE 4

A polyacrylamide of 100 wt portion, particles having a mean diameter of about 30 nm of a conductive carbon black of 80 wt portion, an acrylic binder resin of 100 wt portion and a formalin of 3 wt portion which is used to partially cross link the polyacrylamide, are blended, and the blended materials are mixed with water of 800 wt portion to form a paste of a moisture sensing resistive substance. A water absorption at 25° C. and 65% RH of a film of the moisture sensing resistive substance is 1200%. A nonwoven fabric having a VOID ratio of 60% and a weight per unit area of 15 g/m² is manufactured from an extra fine polyethylene terephthalate fiber having a mean diameter of 1.7 μm, by a melt blow method. The nonwoven fabric is coated with the moisture sensing resistive substance by transfer coating, is dried at 60° C., and then cured at 150° C. for 10 minutes. A thickness of the obtained sheet is 40 mm, and a pick up of the moisture sensing resistive substance in the obtained sheet is 60% o.w.f. A circular sensor having a diameter of 3 mmφ is cut from the obtained sheet. The sensor is adhered through an acrylic group adhesive layer to a predetermined position of a circuit of a printed circuit board supplied by Denki Kagaku Kogyo Co., Ltd., and made of an aluminium plate. A sample XIII of a sensor device in accordance with the present invention and having a constitution illustrated in FIG. 11(a) and FIG. 11(b) is manufactured by the above sensor.

A resistance value before and after a generation of dew condensation, response times at the generation and dissolution of the dew condensation, and dew condensation accuracies thereof for the sample XIII were measured, and are shown in Table 1.

The sample XIII has a feature that the resistance of the sensor changes sharply under a high humidity. A time for a detection of the dew condensation, i.e., the response speed, is fast, i.e., about 30 sec, and a response speed where the sensor is dried after the dissolution of the dew condensation and the value of resistance is recovered is also fast, i.e., about 2 sec to 30 sec. Further the dew condensation accuracy at the time of generating the dew condensation of sample XIII is very fast, i.e., within 1 sec, and the dew condensation accuracy at the time of dissolving the dew condensation is fast, i.e., within 10 sec. Therefore the generation or dissolution of the dew condensation can be accurately measured by this sensor device.

EXAMPLE 5

A polyacrylamide of 100 wt portion, particles having a mean diameter of about 30 nm of a conductive carbon black of 250 wt portion, an acrylic binder resin of 100 wt portion, and a formalin of 3 wt portion which is used to partially cross link the polyacrylamide, are blended, and the blended materials are mixed with water of 800 wt portion to form a paste of a moisture sensing resistive substance. A water absorption at 25° C. and 65% RH of a film of the moisture sensing resistive substance is 1100%. A nonwoven fabric having a VOID ratio of 60% and a weight per unit area of 15 g/m² is manufactured from an extra fine polyethylene terephthalate fiber having a mean diameter of 1.7 μm, by a melt blow method. The nonwoven fabric is coated with the moisture sensing resistive substance by transfer coating, is dried at 60°, and then cured at 150° C. for 10 minutes. A thickness of the obtained sheet is 48 mm, and a pick up of the moisture sensing resistive substance in the obtained sheet is 60% o.w.f.

A sample XIV of a sensor device in accordance with the present invention and having a constitution illustrated in FIG. 9(a) is manufactured by the above sheet.

Figure 5:
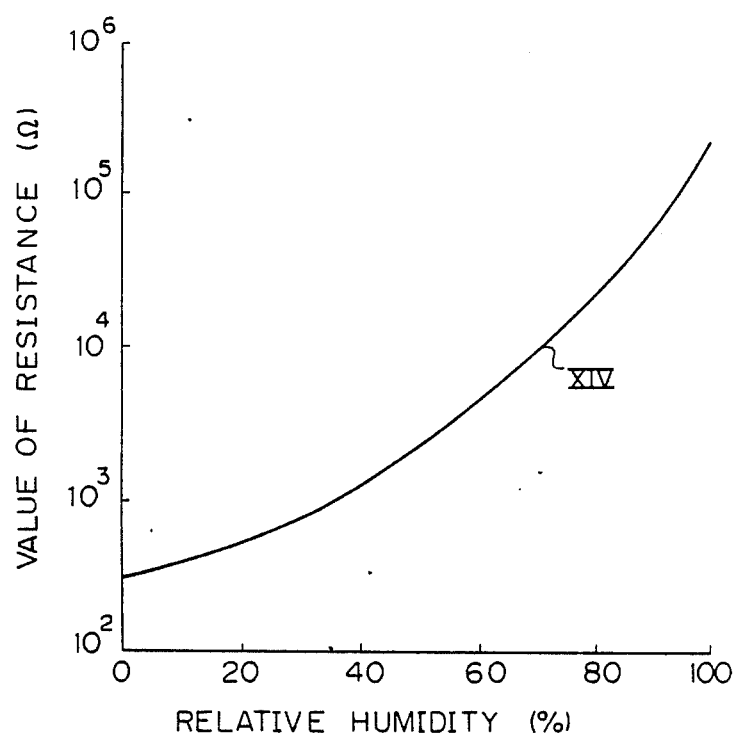
FIG. 5 is the same graph of another sample of the moisture and dew-detection sensor in accordance with the present invention as that illustrated in FIG. 3.

A resistance value before and after a generation of dew condensation, response times upon a generation and dissolution of the dew condensation, and dew condensation accuracies thereof for sample XIV were measured, and are shown in Table 1. Further a change of a resistance value of sample XIV under various relative humidity conditions is illustrated in FIG. 5. As can be seen from FIG. 5, sample XIV has a feature that a resistance is increased gradually from 300 Ω and 200 kΩ in a range of relative humidity between 0% and 100%.

COMPARATIVE EXAMPLE 1

A conventional well-known dew consideration sensor device is prepared, to compare the characteristics thereof with the characteristics of the sensor devices in Example 1. This conventional sensor device is a membrane type sensor device comprising a base plate of an alumina ceramic having a thickness of 0.7 mm and a heat conductivity of 0.03 cal/cm.s.k, a comb-shaped electrode attached to the base plate and connected to lead wires, and a film of a hygroscopic resin having a thickness of about 5 μm, dispersed with conductive carbon black, and covering the two electrodes.

A resistance value before and after a generation of dew condensation, response times at the generation and dissolution of the dew condensation, and dew condensation accuracies thereof for this comparative example 1 were measured, and are shown in Table 1. Further a change of the resistance with time for the comparative example 1 is illustrated in FIG. 4(c).

As can be seen from Table 1 and FIG. 4(c), a time for a detection of the dew condensation, i.e., the response speed of the comparative example 1, is slow, i.e., about one and half minutes, and the resistance value of the comparative example 1 decreases one and half minutes before the dew condensation on the aluminium plate and a surface of the sensor dissolve. Therefore it is impossible to exactly detect the dew state by this comparative example 1.

COMPARATIVE EXAMPLE 2

A sensor of a comparative example 2 is prepared by immersing a paper filter of a cellulose fiber supplied by Toyo Roshi Co., Ltd. in an Indian ink for 5 minutes and allowing to dry. The comparative example 2 of the sensor device is manufactured from the above paper filter by the same method as used in example 4.

A resistance value before and after a generation of dew condensation, response times at the generation and dissolution of the dew condensation, and dew condensation occurrences thereof for this comparative example 2 were measured, and are shown in Table 1. Further a change of the resistance with time for the comparative example 1 is illustrated in FIG. 4(c).

As can be seen from Table 1 and FIG. 4(c), a time for a detection of the dew condensation is very slow. Namely, two and half minutes elapse from a start of the dew condensation to a time when a maximum reference value is obtained, and a resistance value of the comparative example 2 decreases after two minutes; 40 second before the dissolution of the dew condensation, and since water absorbed in the absorption fiber is not likely to evaporate, even if the sensor device is kept in this environment for 10 minutes or more, the resistance value is not returned to the original value of the sensor device.

TABLE 1

| | Sample Number | Fabric | Diameter of Fiber (μm) | VOID Ratio | *Conductive Particle (wt Portion) | Pick up (% o.w.f) | Type of Sensor Device | Mean Value of Resistance at Dew Condensation | | At Generation of Dew Condensation | | At Dissolution of Dew Condensation | |
|---|---|---|---|---|---|---|---|---|---|---|---|---|---|
| | | | | | | | | Before | After | Response Time | Accuracy | Response Time | Accuracy |
| Example 1 | I | Non Woven Fabric | 1.7 | 60 | 80 | 61 | FIG. 9(a) | 15 kΩ | 2.4 MΩ | −20 sec | −1 sec | −2 min 30 sec | −10 sec |
| | II | Non Woven Fabric | 1.7 | 60 | 80 | 61 | FIG. 9(b) | 14 kΩ | 2.5 MΩ | −20 sec | −1 sec | −2 min 30 sec | −10 sec |
| | III | Non Woven Fabric | 8.0 | 55 | 80 | 55 | FIG. 9(b) | 12 kΩ | 2.4 MΩ | −30 sec | 1 sec | −2 min 40 sec | −25 sec |
| | IV | Non Woven Fabric | 27.0 | 48 | 80 | 55 | FIG. 9(b) | 12 kΩ | 2.5 MΩ | −35 sec | 1-2 sec | −2 min 40 sec | −28 sec |
| | V | Non Woven Fabric | 35.0 | 30 | 80 | 60 | FIG. 9(b) | 15 kΩ | 2.5 MΩ | −40 sec | 2 sec | −2 min 50 sec | −30 sec |
| | VI | Woven Fabric | 27.0 | 16 | 80 | 62 | FIG. 9(b) | 11 kΩ | 2.4 MΩ | 1 min | 3 sec | −3 min | −35 sec |
| Example 3 | VII | Non Woven Fabric | 2.0 | 50 | 100 | 5 | FIG. 10 | 550 kΩ | 4.3 MΩ | −20 sec | −1 sec | −1 min | −10 sec |
| | VIII | Non Woven Fabric | 2.0 | 50 | 100 | 15 | FIG. 10 | 70 kΩ | 3.5 MΩ | −20 sec | −1 sec | −1 min | −10 sec |
| | IX | Non Woven Fabric | 2.0 | 50 | 100 | 34 | FIG. 10 | 40 kΩ | 3.3 MΩ | −20 sec | −1 sec | −1 min 30 sec | −10 sec |
| | X | Non Woven Fabric | 2.0 | 50 | 100 | 55 | FIG. 10 | 16 kΩ | 2.5 MΩ | −20 sec | −1 sec | −1 min 30 sec | −10 sec |
| | XI | Non Woven Fabric | 2.0 | 50 | 100 | 93 | FIG. 10 | 11 kΩ | 2.2 MΩ | −25 sec | 1-2 sec | −2 min | −24 sec |
| | XII | Non Woven Fabric | 2.0 | 50 | 100 | 122 | FIG. 10 | 9 kΩ | 1.0 MΩ | −30 sec | 5 sec | −3 min | −30 sec |
| Example 4 | XIII | Non Woven Fabric | 1.7 | 60 | 80 | 60 | FIG. 11 | 15 kΩ | 2.4 MΩ | −30 sec | −1 sec | −2 min 30 sec | −10 sec |
| Example 5 | XIV | Non Woven Fabric | 1.7 | 60 | 250 | 60 | FIG. 9(a) | 5 kΩ | 200 kΩ | −20 sec | −1 sec | −2 min 30 sec | −10 sec |
| Example | XV | Non Woven Fabric | 2.0 | 50 | 120 | 55 | FIG. 9(c) | 9.5 kΩ | 2.6 MΩ | −20 sec | −1 sec | −1 min 30 sec | −10 sec |
| Comparative Example 1 | I | — | — | 0 | — | — | Combed Shape Electrod | 2 kΩ | 2.0 MΩ | −1 min 30 sec | −45 sec | −4 min 30 sec | −1 min 30 sec |
| Comparative Example 2 | II | Paper | 40 | 50 | — | 5 | FIG. 11 | 8.1 kΩ | 98 kΩ | −2 min 30 sec | −40 sec | More than 10 min | −2 min 40 sec |

*wt portion of Conductive Particle against a hygroscopic high polymer.

We claim:

1. A moisture and dew-detection sensor comprised of a nonwoven fabric and a moisture sensing resistive substance adhered in a substantially continuous and dispersed state to said nonwoven fabric, said moisture sensing resistive substance including a mixture of a non-ionic hygroscopic high polymer and a conductive particle, and a plurality of continuous fine voids formed therein.

2. A moisture and dew-detection sensor according to claim 1, wherein said conductive particle is a carbon black.

3. A moisture and dew-detection sensor according to claim 1, wherein said nonwoven fabric is composed of an extra fine fiber having a diameter of 30 $\mu$m or less.

4. A moisture and dew-detection sensor according to claim 1, wherein a pick up of said moisture sensing resistive substance against said fabric is between 10% o.w.f. and 100% o.w.f.

5. A moisture and dew-detection sensor according to claim 1, wherein said moisture sensing resistive substance is applied from a side of said fabric, so that a quantity of the moisture sensing resistive substance on said side of the fabric is greater than that on an opposite side of the fabric.

6. A moisture and dew-detection sensor according claim 1, wherein a VOID rate of said fabric is between 10% and 95%.

7. A moisture and dew-detection sensor according to claim 1, including electrodes attached to at least two portions of said sensor and means for mounting said sensor to a substance to be detected.

8. A moisture and dew-detection sensor device according to claim 7, wherein said sensor mounting means is a plate-like member having a good heat conductivity and adhered through an insulating layer to said sensor and provided with said electrodes thereon.

9. A moisture and dew-detection sensor device according to claim 8, wherein said plate-like member having a good heat conductivity is a printed circuit board made of a metal plate.

10. A moisture and dew-detection sensor according to claim 7, including circuit means for detecting a change of a resistance value of said sensor and outputting said change as an electrical signal.

* * * * *